United States Patent [19]

Lerman et al.

[11] Patent Number: 5,672,755
[45] Date of Patent: Sep. 30, 1997

[54] PROCESS FOR THE PURIFICATION OF (RR-SS)-2-DIMETHYL-AMINOMETHYL-1-(3-METHOXYPHENYL)CYCLOHEXANOL AND ITS SALTS

[75] Inventors: Ori Lerman, Ramat Gan; Michael Tennenbaum, Rosh Haayin; Erez Gal; Joseph Kaspi, both of Givataim, all of Israel

[73] Assignee: Chemagis Ltd., Bnei Brak, Israel

[21] Appl. No.: 746,575

[22] Filed: Nov. 14, 1996

[30] Foreign Application Priority Data

Dec. 7, 1995 [IL] Israel ........................................ 116281

[51] Int. Cl.⁶ .................................................... C07C 209/82
[52] U.S. Cl. ........................... 564/425; 564/424; 564/437; 564/438
[58] Field of Search ................................. 564/424, 425, 564/437, 438

[56] References Cited

U.S. PATENT DOCUMENTS 3,652,589  3/1972  Flick ............................... 260/326.5 M
5,414,129  5/1995  Cherkez .............................. 564/425

*Primary Examiner*—Brian M. Burn
*Assistant Examiner*—Jean F. Vollano
*Attorney, Agent, or Firm*—Darby & Darby

[57] ABSTRACT

The invention provides a process for the purification and isolation of (RR,SS)-2-dimethylaminomethyl-1-(3-methoxyphenyl)cyclohexanol from mixtures also containing the (RS,SR) isomer comprising reacting the above mixture in a solvent at elevated temperature under acidic conditions, whereby the (RS,SR) isomer is selectively converted to the (RR,SS) isomer, 1-(3-methoxyphenyl)-2-dimethylaminomethylcyclohex-6-ene, 1-(3-methoxyphenyl)-2-dimethyl-aminomethylcyclohex-1-ene or a mixture thereof, selectively precipitating the desired (RR,SS) isomer as an amine acid salt, and recrystallizing the purified product.

14 Claims, No Drawings

PROCESS FOR THE PURIFICATION OF (RR-SS)-2-DIMETHYL-AMINOMETHYL-1-(3-METHOXYPHENYL)CYCLOHEXANOL AND ITS SALTS

The present invention relates to a process for the purification of (RR,SS)-2-dimethylaminomethyl-1-(3-methoxyphenyl)cyclohexanol hydrochloride, also known as Tramadol from its (RS,SR) isomer and other undesirable products. More particularly the present invention is based on the newly discovered observation that the (RS,SR) isomer undergoes dehydration under certain conditions, while the (RR,SS) isomer remains practically intact.

Tramadol is a well-established pain-killer invented by Gruenenthal GmbH, Germany, used as a non-addictive analgestic and sold under different trade names such as Tramal, Crispin or Tramundin.

The synthesis of Tramadol is described in U.S. Pat. No. 3,652,589 and in British pat. No. 992399.

The standard commercial synthesis of Tramadol consists of a Grignard reaction between 2-dimethylaminomethylcyclohexanone and 3-methoxyphenylmagnesium bromide (Equation 1).

From the reaction nature, it is clear that both isomers (RR,SS) (Structure 1) and (RS,SR) (Structure 2) are obtained in variable ratios, depending on the reaction conditions.

EQUATION 1

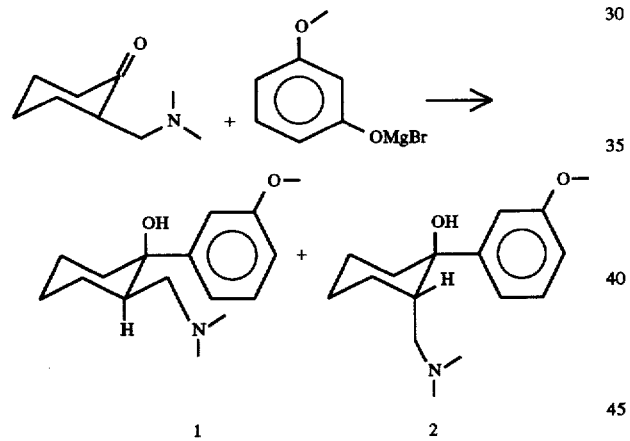

The original patents assigned to Gruenenthal GmbH describe the isolation of the pure (RR,SS) isomer as follows: The complex mixture of products containing both isomers of Tramadol obtained from the Grignard reaction is distilled under high vacuum. Both isomers distill at 138°–140°, (0.6 mmHg). The distillate is dissolved in ether, and the solution is treated with gaseous HCl The resulting mixture of Tramadol hydrochloride isomers is precipitated and filtered, usually this mixture contains about 20% of the (RS,SR) isomer.

The mixture of isomers is then refluxed twice with five volumes of moist dioxane, and filtered. The cake obtained consists of pure (RR,SS) isomer, while the residual solution consists of "a mixture of about 20% to 30% of the cis (i.e. RS,SR) isomer and about 70% to 80%) of the trans (i.e. RR,SS) isomer which cannot be further separated by boiling dioxane" (U.S. Pat. No. 3,652,589—Example 2).

Dioxane, used in large quantities in this process, possesses many undesirable properties. It has recently been listed as Category 1 carcinogen by OSHA. (Kirk & Othmer, 3rd edition, vol. 9, page 386) and it is known to cause CNS depression and liver necrosis (ibid. vol. 13, page 267). In addition, it tends to form hazardous peroxides (ibid. vol. 17, page 48).

As a result, the concentration of dioxane in the final product has been strictly limited to several ppb's, and the DAC (1991) restricted the level of dioxane in Tramadol to 500 ppb.

Another separation method patented by Chemagis Ltd. (IL 103096) takes advantage of the fact that the precipitation of the (RR,SS) isomer of Tramadol from its solution in medium chained alcohols ($C_4$–$C_8$) occurs faster than the precipitation of the (RS,SR) isomer which tends to separate later.

The main disadvantage of this method is that the time interval between the end of separation of the (RR,SS) isomer and the start of the (RS,SR) isomer separation is variable, and seems to depend sharply on the composition of the crude mixture. Therefore, variations in the yield and the quality of the product often occur. Furthermore, about 40% of the (RR,SS) isomer does not separate and remains in solution, along with the (RS,SR) isomer. This mixture cannot be further purified by this method.

After performing a series of experiments in order to investigate the chemical properties of both isomers of Tramadol, it has now been surprisingly found, that the isomers exhibit considerable differences in their chemical behavior, namely the (RS,SR) isomer has been found to be considerably more reactive towards dehydration than the (RR,SS) isomer. Practically, when a mixture of both isomers of Tramadol is heated with a strong acid in an organic or aqueous medium, the (RS,SR) isomer undergoes selective dehydration, while the (RR,SS) isomer remains intact. The main dehydration product is 1-(-3-methoxyphenyl)-2-dimethylaminomethyl-cyclohex-6-ene (3), while minor quantities of 1-(3-methoxyphenyl)-2-dimethylaminomethyl cyclohex-1-ene.

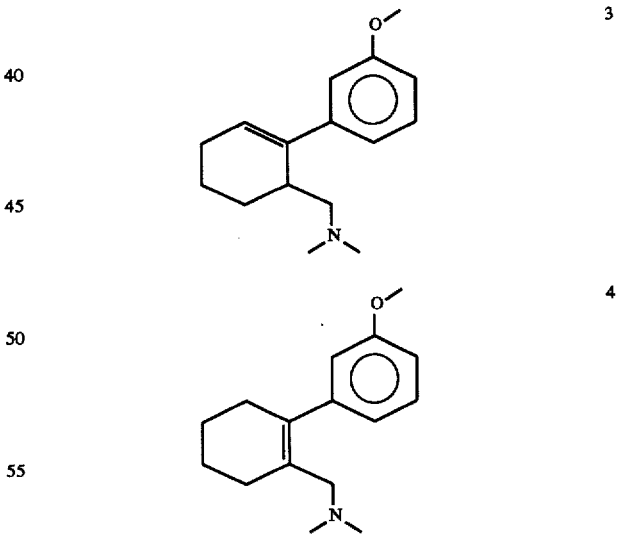

Once most of the (RS,SR) isomer is converted to the dehydrated compounds, the resulting (RR,SS) isomer can be easily purified from the other compounds by simple recrystallization.

In retrospect, looking at the structure of both Tramadol isomers, it is evident why the (RS,SR) isomer is more susceptible to dehydration.

The proton attached to the nitrogen of the protonated (RR,SS) isomer of Tramadol is capable of forming a stable hydrogen bond with the oxygen atom of the hydroxyl group, (see FIG. 1), thus a second protonation on the hydroxyl group (which is the first intermediate of the dehydration chain) is less likely to occur. In the (RS,SR) isomer, there is no possible way of forming a stable intramolecular hydrogen bond, therefore, a second protonation can smoothly take place, followed by water elimination (see FIG. 2.).

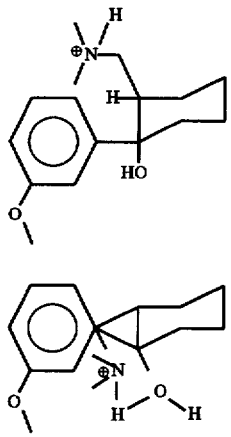

FIG. 1

FIG. 2

Furthermore, when the reaction is carried out in aqueous medium, a certain amount of the (RS,SR) isomer, up to 50%, is converted to the (RR,SS) form. This may, of course, increase the efficiency of the process.

Thus, according to the present invention there is now provided a process for the purification and isolation of (RR,SS)-2-dimethylaminomethyl-1-(3-methoxyphenyl) cyclohexanol from mixtures which also contain the (RS,SR) isomer comprising: (a) reacting the above mixture in a solvent at elevated temperature under acidic conditions, whereby the (RS,SR) isomer is selectively converted to the (RR,SS) isomer, 1-(-3-methoxyphenyl)-2-dimethylaminomethyl cyclohex-6-ene, 1-(3-methoxyphenyl)-2-dimethyl-aminomethyl cyclohex-1-ene or a mixture thereof; (b) selectively precipitating the desired (RR,SS) isomer as an amine acid salt; and (c) recrystallizing the purified product.

Treatment with aqueous acidic solution can be applied in order to purify mixtures of Tramadol isomers considered hitherto to be unseparable, like the residues obtained from the purification process using dioxane, as described in U.S. Pat. No. 3,653,589, or from the purification process with medium chained alcohols, as described in Israeli patent 103096 corresponding to U.S. Pat. No. 5,414,129. Furthermore, pure (RS,SR) isomer can be partially converted to the desired (RR,SS) isomer when treated under the above-mentioned conditions.

The general purification procedure consists of heating the mixture of Tramadol isomers obtained from the Grignard reaction between 2-dimethylaminomethyl cyclohexanone and 3-methoxphenylmagnesium-bromide with strong acid in aqueous medium. The resulting mixture is brought to pH 13, extracted with toluene and the organic phase is evaporated under reduced pressure. The resulting oil is treated with HCl solution in 2-propanol, and cooled to 5° C. The (RR,SS) isomer of Tramadol separates exclusively, while most of the other ammonium salts [including the (RR,SS) isomer, and the hydrochlorides of the dehydrated derivatives of Tramadol] stay in solution. The crude (RR,SS) isomer obtained can be purified by recrystallization.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

923 gr. of solution obtained from Grignard reaction between 2-dimethylaminomethylcyclohexanone and 3-methoxyphenylmagnesium bromide is evaporated under reduced pressure until no solvent distillation is observed. 212 gr. of thick oil containing 43.5% of (RR,SS) Tramadol and 8% of (RS,SR) Tramadol is obtained. The isomer ratio is about 1:5.5. 530 gr. of water and 180 gr. of 4-toluenesulfonic acid monohydrate are added and the mixture is heated to 100° C. for 2 hours. The mixture is cooled and brought to pH 8, 100 gr. of solid potassium carbonate and 250 ml. of toluene are added thereinto, and the phases are separated.

The organic phase is evaporated and 173 gr. of dark oil containing 48.7% of the (RR,SS) isomer and 2.5% of the (RS,SR) isomer is obtained. The isomer ration is 1:20 and the efficiency of the (RR,SS) isomer resolving is 92%.

EXAMPLE 2

172 gr. of the crude product obtained from Example 1 was dissolved in 150 ml. of 2-propanol, 110 ml. of 23% solution of the HCl in 2-propanol is gradually added while the temperature is kept below 25° C. The mixture is then stirred and cooled to 5° C. for 10 hours. The (RR,SS) isomer of Tramadol is separated almost in pure form. The crude product is recrystallized from 2-propanol.

EXAMPLE 3

1000 gr. of mixture obtained from Grignard reaction between 2-diethylaminomethyl cyclohexanone and 3-methoxyphenylmagnesium bromide is evaporated under reduced pressure until no solvent distillation is observed. 225 gr. of dark oil containing 43.5% of (RR,SS) Tramadol and 8% of (RS,SR) Tramadol is obtained. The mutual ratio of both isomers of tramadol is 1:5.5. 60 ml of toluene and 18 gr. of 4-toluenesulfonic acid monohydrate are added and the mixture is heated to 90° C. for 2 hours. The reaction is worked up in the same manner as described in Example 1. The isomer ration is 1:8 and the efficiency of the (RR,SS) isomer is 95%.

EXAMPLE 4

The solution obtained after the Grignard is treated with 4-toluenesulfonic acid in the same manner as described in Example 1, but the reaction mixture is heated to 90° C. for 2½ hours. At the end of the reaction the mutual isomer ration is 1:18 and the efficiency of the (RR,SS) isomer resolving is 102%. The product is worked up as described in Example 2 to give the final product.

EXAMPLE 5

The solution obtained after the Grignard reaction is treated with 4-toluenesulfonic acid in the same manner as described in Example 1, but the reaction mixture is heated to 75° C. and the reaction is stopped after 4 hours. At the end of the reaction the isomer was 1:8 and the efficiency of the (RR,SS) isomer resolving is 99%.

EXAMPLE 6

To 8.8 grams of pure (RS,SR) isomer of Tramadol are added 25 ml of water and 10 gr. of 4-toluenesulfonic acid monohydrate. The mixture is heated to 95° C. for 2 hours. The reaction is stopped and worked up in the same manner as described in Example 1. 8 gr. of oil consisting of 52.8% of (RR,SS) Tramadol, 5% of (RS,SR) Tramadol and 37.8% of 2-dimethylaminomethyl-1-(3-methoxyphenyl) cyclohex-6-ene.

EXAMPLE 7

3600 ml of filtrate containing 7% of (RR,SS) Tramadol and 1.7% of (RS,SR) Tramadol dissolved in a mixture of primary alcohols obtained as mother liquor from the purifying process for Tramadol as described in Israeli Pat. 103096 is evaporated to about one half of its volume, and the dark viscous solution obtained is extracted with 2×1500 ml of water.

The aqueous phase is brought to pH 7 with 40% NaOH solution then 500 gr. of solid potassium carbonate and 1500 ml of toluene are added.

The mixture is stirred, the layers separated, and the organic layer was evaporated to dryness.

230 gr. 4-toluenesulfonic acid monohydrate and 456 ml. of water are added to the residue, and the mixture is heated to 90° C. for 2½ hours. The reaction is stopped and worked up in the same manner as described in Example 1. The mutual ration between the isomers is 1:20, and the yield up to this point is 76%. Pure (RR,SS) Tramadol was resolved from the dark oil as described in Example 2.

EXAMPLE 8

71 gr. of isomers mixture containing 51 gr. of (RR,SS) Tramadol and 20 gr. of (RS,SR) Tramadol obtained as an inseparable mixture obtained as a result of the isomers purification method described in U.S. Pat. No. 3,652,589 was converted to the corresponding base mixture by treating with 30% $K_2CO_3$ mixture. 62 gr. of mixture is obtained.

The mixture is heated to 90° C. with 90 gr. 4-toluenesulfonic acid and 250 ml $H_2O$ for 2½ hours and the mixture was worked up as described in Example 2.

The mutual ratio between the isomers is 1:20 and the efficiency of the isomer resolving is 111%.

EXAMPLE 9

A mixture prepared from 5 gr. (RR,SS) Tramadol and 5 gr. (RS,SR) Tramadol is heated for 3 hours to 90° C. with 50 ml. of water and 15 gr. of 4-toluenesulfonic acid monohydrate for 2 hours. The reaction is stopped and worked up in the same manner as described in Example 1.

The mutual ratio between the isomers is 1:18 and the efficiency of the isomer resolving is 122%.

EXAMPLE 10

923 gr. of solution obtained from Grignard reaction between 2-dimethylaminomethylcyclohexanone and 3-methoxyphenylmagnesium bromide is evaporated under reduced pressure until no solvent distillation is observed. 215 gr. of thick oil is obtained. 250 ml of 25% aqueous solution of sulfuric acid is introduced thereinto, and the mixture is heated to 90° C. for 2 hours. The mixture is brought to pH 11 with solid potassium carbonate and extracted with toluene.

The mutual ratio between the isomers is 1:18 and the efficiency of the isomers resolving is 120%.

EXAMPLE 11

115 gr. of thick oil obtained from Grignard reaction between 2-dimethylaminomethylcyclohexanone and 3-methoxyphenylmagnesium bromide containing (RR,SS) and RS,SR) isomers of Tramadol in the mutual ration of 1:5.5. The oil is heated to 90° C. with 250 ml of 50% solution of phoshoric acid for 2.5 hours. The dark oil resulted contains both isomers of Tramadol in the ratio of 1:18. The efficiency of the isomer resolving is 75%.

EXAMPLE 12

115 gr. of thick oil obtained from Grignard reaction between 2-dimethylaminomethylcyclohexanone and 3-methoxyphenylmagnesium-bromide containing (RR,SS) and (RS,SR) isomers of Tramadol in the mutual ratio of 1:5.5. The oil is heated to 90° C. with 250 ml of 70% solution of formic acid for 2.5 hours. The dark oil resulting both isomers of Tramadol, in the ratio of 1:9. The efficiency of the isomer resolving is 66%.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the purification and isolation of (RR,SS)-2-dimethylaminomethyl-1-(3-methoxyphenyl) cyclohexanol from mixtures also containing the (RS,SR) isomer comprising:

a. reacting the above mixture in a solvent at elevated temperature under acidic conditions, whereby the (RS,SR) isomer is selectively converted to the (RR,SS) isomer, 1-(3-methoxyphenyl)-2-dimethylaminomethylcyclohex-6-ene, 1-(3-methoxyphenyl)-2-dimethyl-aminomethylcyclohex-1-ene or a mixture thereof;

b. selectively precipitating the desired (RR,SS) isomer as an amine acid salt; and c. recrystallizing the purified product.

2. A process according to claim 1, wherein the mixture subjected to the treatment is obtained by the reaction of 2-dimethylaminomethylcyclohexanone and 3-methoxyphenylmagnesium bromide.

3. A process according to claim 1, wherein said mixture of isomers is an inseparable mixture of the cis isomer and the trans isomer which cannot be further separated by boiling dioxane.

4. A process according to claim 1, wherein said mixture of isomers is obtained as an inseparable mixture of the cis and trans isomer which cannot be further separated by subjecting it to fractional crystallization by medium $C_3$–$C_8$ alcohols.

5. A process according to claim 1, wherein the reacting substance is pure (RS,SR) 2-dimethylamino-1-(3-methoxyphenyl) cyclohexanol.

6. A process according to claim 1, wherein the reaction is carried out at temperature between 50°–120° C.

7. A process according to claim 1, wherein the reaction is carried out at the boiling point of the reaction mixture.

8. A process according to claim 1, wherein the solvent is water.

9. A process according to claim 1, wherein said acid is sulfuric acid.

10. A process according to claim 1, wherein said acid is 4-toluenesulfonic acid.

11. A process according to claim 1, wherein the precipitation of Step b is carried out using an alcohol and hydrogen chloride.

12. A process according to claim 1, wherein the final precipitation is carried out by recrystallization from an alcohol.

13. A process according to claim 11, wherein the alcohol is 2-propanol.

14. (RR-SS)-2-dimethylaminomethyl-1-(3-methoxyphenyl) cyclohexanol hydrochloride prepared in accordance with claim 1.

* * * * *